US012573500B2

(12) United States Patent
Kyne et al.

(10) Patent No.: US 12,573,500 B2
(45) Date of Patent: Mar. 10, 2026

(54) ASSESSING OPERATOR BEHAVIOR DURING A MEDICAL PROCEDURE

(71) Applicant: KONINKLIJKE PHILIPS N.V., Eindhoven (NL)

(72) Inventors: Sean Joseph Kyne, Brookline, MA (US); Ayushi Sinha, Baltimore, MD (US); Ramon Quido Erkamp, Swampscott, MA (US); Javad Fotouhi, Cambridge, MA (US); Leili Salehi, Waltham, MA (US); Vipul Shrihari Pai Raikar, Somerville, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 126 days.

(21) Appl. No.: 18/374,450

(22) Filed: Sep. 28, 2023

(65) Prior Publication Data

US 2024/0112788 A1 Apr. 4, 2024

Related U.S. Application Data

(60) Provisional application No. 63/411,214, filed on Sep. 29, 2022.

(30) Foreign Application Priority Data

Dec. 1, 2022 (EP) .................................... 22210837

(51) Int. Cl.
G16H 40/20 (2018.01)
G06N 3/0455 (2023.01)
G06N 3/084 (2023.01)

(52) U.S. Cl.
CPC .......... *G16H 40/20* (2018.01); *G06N 3/0455* (2023.01); *G06N 3/084* (2013.01)

(58) Field of Classification Search
CPC ....... G16H 40/20; G06N 3/0455; G06N 3/084
See application file for complete search history.

(56) References Cited

U.S. PATENT DOCUMENTS 9,152,918 B1 10/2015 Mcnair
9,814,420 B2 * 11/2017 Badenes ................ A61B 5/165
(Continued)

FOREIGN PATENT DOCUMENTS

CN 105224872 A 1/2016
NL 2020259 B1 7/2019
(Continued)

OTHER PUBLICATIONS

Parekh, V., Shah, D. & Shah, M. Fatigue Detection Using Artificial Intelligence Framework. Augment Hum Res 5, 5 (2020) (Year: 2020).*

(Continued)

*Primary Examiner* — Matthew L Hamilton

(57) ABSTRACT

A computer-implemented method of assessing operator behavior during a medical procedure involving medical equipment, is provided. The method includes: receiving operator interaction data representing operator interactions with the medical equipment during the medical procedure; inputting the operator interaction data into a machine-learning model; and outputting a characteristic of the operator behavior based on a position of a latent space encoding of the operator interaction data generated by the machine-learning model, with respect to a distribution of latent space encodings of training data representing operator interactions with the medical equipment having known characteristics of the operator behavior.

15 Claims, 5 Drawing Sheets

(56)                   References Cited

U.S. PATENT DOCUMENTS

| | | | |
|---|---|---|---|
| 2015/0364022 A1* | 12/2015 | Dyell | G16H 40/63 |
| | | | 340/573.1 |
| 2019/0304596 A1 | 10/2019 | Padala | |
| 2020/0070838 A1* | 3/2020 | Smith | G08B 25/08 |
| 2020/0184316 A1 | 6/2020 | Kavukcuoglu et al. | |
| 2021/0304875 A1* | 9/2021 | Sevenster | G16H 40/20 |
| 2021/0313052 A1 | 10/2021 | Makrinich et al. | |
| 2022/0233267 A1* | 7/2022 | Shelton, IV | A61B 34/77 |
| 2023/0178248 A1* | 6/2023 | Sinha | G16H 30/40 |
| | | | 705/2 |
| 2024/0320596 A1* | 9/2024 | Shivaraman | G06Q 10/06312 |

FOREIGN PATENT DOCUMENTS

| | | | |
|---|---|---|---|
| WO | 2016149794 A1 | 9/2016 | |
| WO | 2018156192 A1 | 8/2018 | |
| WO | 2020247451 A1 | 12/2020 | |
| WO | 2021209525 A1 | 10/2021 | |

OTHER PUBLICATIONS

Lee et al., "Understanding Keystroke Dynamics for Smartphone Users Authentication and Keystroke Dynamics on Smartphones Built-In Motion Sensors", Applied Cryptography and Noise Resistant Data Security, Special Issue (2018).
Salyers et al., "The Relationship Between Professional Burnout and Quality and Safety in Healthcare: A Meta-Analysis", J Gen Intern Med 32, 475-482 (2017).
Bundy et al., "Burnout among Interventional Radiologists" JVIR 31(4): 607-631 (2020).

* cited by examiner

ASSESSING OPERATOR BEHAVIOR DURING A MEDICAL PROCEDURE

CROSS REFERENCE TO RELATED APPLICATION

This application claims the benefit of U.S. Provisional Application Ser. No. 63/411,214, filed Sep. 29, 2022, and European Patent Application No. 22210837.5 filed Dec. 1, 2022. These applications are incorporated by reference herein.

TECHNICAL FIELD

The present disclosure relates to assessing operator behavior during a medical procedure involving medical equipment. A computer-implemented method, a computer program product, and a system, are disclosed.

BACKGROUND

During medical procedures, many different operators, for example physicians, radiology technicians, nurses, and so forth, interact with the medical equipment that is used in the procedure. For instance, operators may interact with an imaging system in order to set the values of image acquisition parameters and image visualization parameters in order to generate images that help to guide the procedure. Operators may likewise interact with other types of medical equipment such as a contrast agent injector in order to set the values of parameters that control an injection of contrast agent.

By way of an example, a coronary angioplasty procedure typically involves the insertion of a sheath into the groin, wrist or arm, in order to gain arterial access. A catheter is passed through the sheath and is then guided through various blood vessels and into the opening of a coronary artery. This procedure is known as catheterization, and is typically performed under X-ray guidance. During catheterization, a contrast agent is typically injected into the vasculature in order to improve visualization of the blood vessels through which the catheter is inserted. A guidewire is inserted within the catheter and guided to a stenosis on which the angioplasty procedure is to be performed. A balloon is then passed over the guidewire until the stenosis is reached. The balloon is expanded within the stenosis and held in the expanded state for a period of approximately twenty to thirty seconds. This opens-up the stenosis, restoring blood flow. A stent may be used to permanently maintain the artery in the expanded state, and in which case the balloon is expanded within the stent. After the stenosis has been opened-up, the balloon is deflated. A physician then verifies the success of the angioplasty procedure by injecting contrast agent into the vasculature and monitoring blood flow using fluoroscopic imaging. Following successful expansion of the artery, the balloon, guidewire, and catheter are removed from the body.

During such a procedure, a physician may perform the catheterization using a catheter/guidewire manipulator. A nurse may position a patient bed, and control a contrast agent injector to inject the contrast agent. A radiology technician may set the values of image acquisition parameters of an X-ray imaging system such as an orientation, an amount of X-ray dose, an exposure time, a collimation area, and an imaging frame rate. The radiology assistant may also set the values of image visualization parameters that control factors such as a magnification of a displayed X-ray image, or a mapping of pixel intensity values in the displayed X-ray image.

Operator interactions such as those described above are typically performed in accordance with a specified protocol. This provides a degree of predictability in the outcome of the procedure. However, there can be situations in which there are deviations from the specified protocol. Deviations from a specified protocol may occur as a result of behavioral factors such as fatigue, understaffing, or a lack of operators with the correct experience. If such behavior is undetected, the outcome of the procedure may be impacted. For instance, the medical procedure may be complicated, or it may need to be repeated. In some cases, the patient might even be harmed.

Currently, operator behavioral factors that may affect the outcome of the procedure are detected based on operator observations. For instance, a physician may observe an operator using incorrect settings to acquire a medical image. The physician may then conclude that the operator is fatigued. The physician may then make a request for the operator to be replaced. However, this method of assessing operator behavior can be unreliable since it relies on the chance observations of a busy physician. It also distracts the physician from other aspects of the procedure.

Thus, there remains a need to reliably assess operator behavior during a medical procedure.

SUMMARY

According to one aspect of the present disclosure, a computer-implemented method of providing an assessment of operator behavior during a medical procedure involving medical equipment, is provided. The method includes:

receiving, during the medical procedure, operator interaction data representing operator interactions with a user interface device associated with the medical equipment;

inputting the operator interaction data into a machine-learning model, the machine-learning model being trained to generate a latent space encoding of the operator interaction data; and outputting, as the assessment of the operator behavior, a characteristic of a set of known characteristics of operator behavior, based on a position of the latent space encoding of the operator interaction data generated by the machine-learning model, with respect to a distribution of latent space encodings of training data representing operator interactions with the user interface device, the distribution being associated with one of the set of known characteristics of the operator behavior.

The above method is based on the insight that during a medical procedure involving medical equipment, characteristics of an operator's behavior may be manifested in their interactions with a user interface device associated with the medical equipment. In the above method, operator interaction data that is generated during a medical procedure, is inputted into a trained machine-learning model. The machine-learning model generates a latent space encoding of the operator interaction data. An assessment of the operator behavior is then outputted based on a position of the latent space encoding with respect to a distribution of latent space encodings of training data representing operator interactions with the user interface device. In particular, a known characteristic of the operator behavior being associated with a specific distribution of latent space encodings may be established as the assessment of operator behavior. In other words, the method determines, as an assessment of operator behavior, one characteristic of a set of characteristics of the operator behavior for the procedure by comparing the latent space encoding for the current procedure to latent space encodings of training data for which the operator behavior characteristic is known. In so doing, the method provides a reliable assessment of operator behavior. The set of known characteristics of operator behavior may include characteristics such as "typical behavior", "inexperience", "understaffing", "unexpected behavior", and so forth, which may therefore be identified using the method. Characteristics of the operator behavior that may adversely affect the procedure may then be notified to the operators, permitting corrective action to be taken. In so doing, risks such as complications to the medical procedure, the need to repeat the medical procedure, and the risk of harm to a patient, may be reduced.

Further aspects, features, and advantages of the present disclosure will become apparent from the following description of examples, which is made with reference to the accompanying drawings.

DETAILED DESCRIPTION

Figure 1:
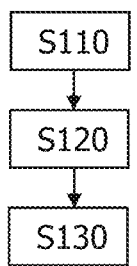
FIG. 1 is a flowchart illustrating an example of a computer-implemented method of assessing operator behavior during a medical procedure involving medical equipment, in accordance with some aspects of the present disclosure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, features described in relation to a computer implemented method, may be implemented in a computer program product, and in a system, in a corresponding manner.

In the following description, reference is made to computer-implemented methods that involve assessing operator behavior during a medical procedure involving medical equipment. Reference is made to examples in which the medical procedure is a coronary angioplasty procedure. Reference is made to examples of this procedure in which the medical equipment includes a projection X-ray imaging system and a contrast agent injector. However, it is to be appreciated that these serve only as examples, and that the methods may in general be used with any type of medical procedure that involves medical equipment, and that the medical equipment may in general be any type of medical equipment relating to the procedure. For instance, the medical equipment may include medical imaging equipment such as a projection X-ray imaging system, a computed tomography "CT" imaging system, a positron emission tomography "PET" imaging system, a single photon emission computed tomography "SPECT" imaging system, an ultrasound imaging system, an intravascular ultrasound "IVUS" imaging system, an optical coherence tomography "OCT" imaging system, and so forth. The medical equipment may also include other types of medical equipment such as a contrast agent injector, a ventilator, a defibrillator, a robotic device controller or manipulator, an aspiration device for removing blood clots, or a laser (atherectomy, or optical position determination) device.

It is noted that the computer-implemented methods disclosed herein may be provided as a non-transitory computer-readable storage medium including computer-readable instructions stored thereon, which, when executed by at least one processor, cause the at least one processor to perform the method. In other words, the computer-implemented methods may be implemented in a computer program product. The computer program product can be provided by dedicated hardware, or hardware capable of running the software in association with appropriate software. When provided by a processor, the functions of the method features can be provided by a single dedicated processor, or by a single shared processor, or by a plurality of individual processors, some of which can be shared. The functions of one or more of the method features may for instance be provided by processors that are shared within a networked processing architecture such as a client/server architecture, a peer-to-peer architecture, the Internet, or the Cloud.

The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, there remains a need to reliably assess operator behavior during a medical procedure.

Figure 2:
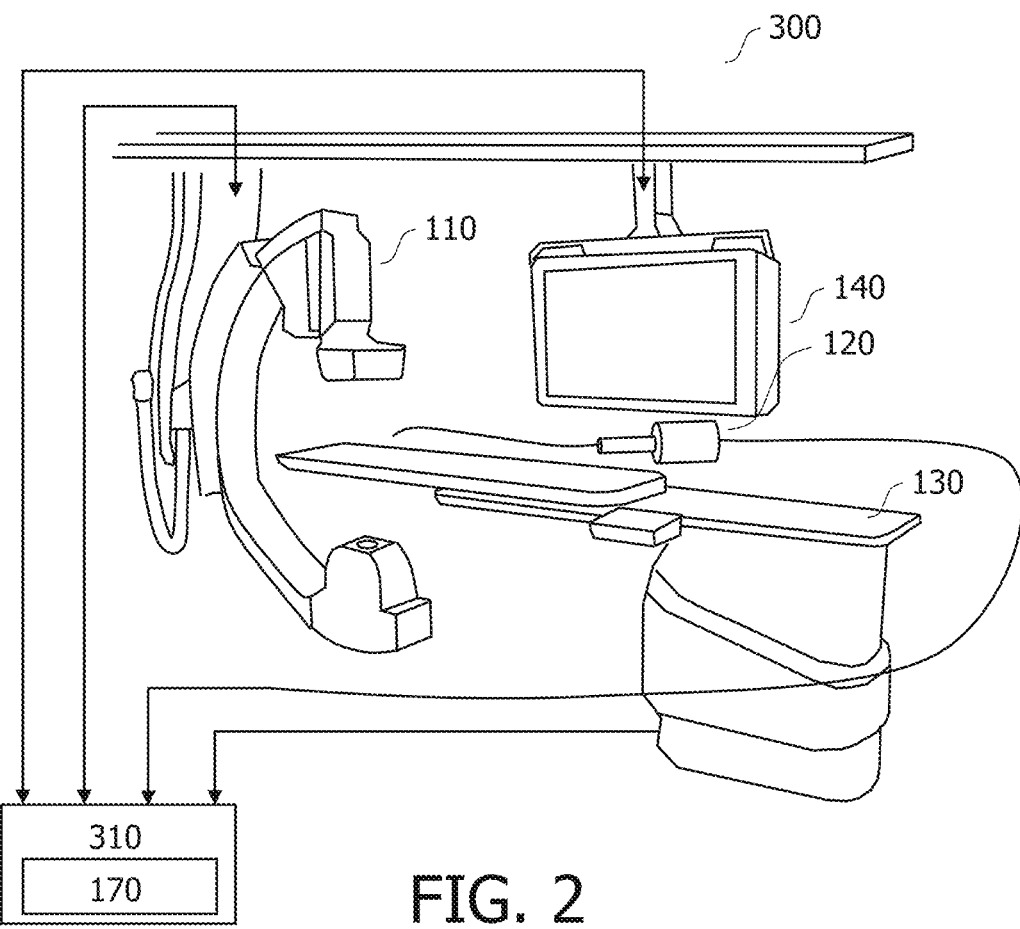
FIG. 2 is a schematic diagram illustrating an example of a system 300 for assessing operator behavior during a medical procedure involving medical equipment, in accordance with some aspects of the present disclosure.

FIG. 1 is a flowchart illustrating an example of a computer-implemented method of assessing operator behavior during a medical procedure involving medical equipment, in accordance with some aspects of the present disclosure. FIG. 2 is a schematic diagram illustrating an example of a system 300 for assessing operator behavior during a medical procedure involving medical equipment, in accordance with some aspects of the present disclosure. Operations described in relation to the method illustrated in FIG. 1, may also be performed by the system 300 illustrated in FIG. 2. Likewise, operations described in relation to the system 300 may also be performed in the method described with reference to FIG. 1. With reference to FIG. 1, the computer-implemented method of assessing operator behavior during a medical procedure involving medical equipment, includes:

receiving S110, during the medical procedure, operator interaction data 150 representing operator interactions 160 with a user interface device associated with the medical equipment;

inputting S120 the operator interaction data 150 into a machine-learning model (e.g., neural network) 170, the machine-learning model being trained to generate a latent space encoding 180 of the operator interaction data; and outputting S130, as an assessment of the operator behavior, a characteristic of a set of known characteristics of the operator behavior, based on a position of the latent space encoding 180 of the operator interaction data generated by the machine-learning model 170, with respect to a distribution $190_1$, $190_2$ of latent space encodings of training data representing operator interactions with the user interface device, the distribution being associated with one of the set of known characteristics $200_1$, $200_2$ of the operator behavior.

The above method is based on the insight that during a medical procedure involving medical equipment, characteristics of an operator's behavior are manifested in their interactions with the medical equipment. In the above method, operator interaction data that is generated during a medical procedure, is inputted into a trained machine-learning model. The machine-learning model generates a latent space encoding of the operator interaction data. An assessment of the operator behavior is then outputted based on a position of the latent space encoding with respect to a distribution of latent space encodings of training data representing operator interactions with the user interface device. In particular, a known characteristic of the operator behavior being associated with a specific distribution of latent space encodings may be established as the assessment of operator behavior. In other words, the method determines, as an assessment of operator behavior, one characteristic of a set of characteristics of the operator behavior for the procedure by comparing the latent space encoding for the current procedure to latent space encodings of training data for which the operator behavior characteristic is known. In so doing, the method provides a reliable assessment of operator behavior. The set of known characteristics of operator behavior may include characteristics such as "typical behavior", "inexperience", "understaffing", "unexpected behavior", and so forth, which may therefore be identified using the method. Characteristics of the operator behavior that may adversely affect the procedure may then be notified to the operators, permitting corrective action to be taken. In so doing, risks such as complications to the medical procedure, the need to repeat the medical procedure, and the risk of harm to a patient, may be reduced.

The method illustrated in FIG. 1 may be used in various types of medical procedures. By way of an example, the method may be used in a coronary angioplasty procedure. A coronary angioplasty procedure typically involves the insertion of a sheath into the groin, wrist or arm, in order to gain arterial access. A catheter is passed through the sheath and is then guided through various blood vessels and into the opening of a coronary artery. This procedure is known as catheterization, and is typically performed under X-ray guidance. During catheterization, a contrast agent is typically injected into the vasculature in order to improve visualization of the blood vessels through which the catheter is inserted. A guidewire is inserted within the catheter and guided to a stenosis on which the angioplasty procedure is to be performed. A balloon is then passed over the guidewire until the stenosis is reached. The balloon is expanded within the stenosis and held in the expanded state for a period of approximately twenty to thirty seconds. This opens-up the stenosis, restoring blood flow. A stent may be used to permanently maintain the artery in the expanded state, and in which case the balloon is expanded within the stent. After the stenosis has been opened-up, the balloon is deflated. A physician then verifies the success of the angioplasty procedure by injecting contrast agent into the vasculature and monitoring blood flow using fluoroscopic imaging. Following successful expansion of the artery, the balloon, guidewire, and catheter are removed from the body.

During such a procedure, a physician may perform the catheterization using a catheter/guidewire manipulator. A nurse may position a patient bed, and control a contrast agent injector to inject the contrast agent. A radiology technician may set the values of image acquisition parameters of an X-ray imaging system such as an orientation, an amount of X-ray dose, an exposure time, a collimation area, and an imaging frame rate. The radiology assistant may also set the values of image visualization parameters that control factors such as a magnification of a displayed X-ray image, or a mapping of pixel intensity values in the displayed X-ray image.

With reference to FIG. 1, in the operation S110, operator interaction data 150 is received. The operator interaction data 150 represents operator interactions 160 with the user interface device during the medical procedure.

One type of interaction that may be performed by an operator during a medical procedure is to set a value of a parameter of the medical equipment used during the medical procedure through the user interface device. With reference to the example coronary angiography procedure describe above, the medical equipment may include equipment such as a catheter/guidewire manipulator, an X-ray imaging system, a patient table, a contrast agent injector, and so forth. One example of a parameter of the medical equipment that may be set by an operator in this example procedure relates to the catheter/guidewire manipulator. An operator may, through the user interface device, set a value of a parameter of the catheter/guidewire manipulator in order to control a position of the catheter/guidewire in the vasculature of a patient. The parameter of the catheter/guidewire manipulator may control a translation, or a rotation, of the catheter/guidewire, for example. For instance, the parameter may provide a specified amount of translation or rotation, or a specified rate of translation or rotation. The parameter may alternatively control an amount of bending, or a direction of bending of the catheter/guidewire. Another example of a parameter of the medical equipment that may be set by an operator in this example procedure relates to the X-ray imaging system. An operator may, through the user interface device, set a value of a parameter of the X-ray imaging system in order to control the acquisition of X-ray images of a region of interest in the patient during the medical procedure. The parameter of the X-ray imaging system may control a factor such as an orientation of the X-ray imaging system with respect to a region of interest, an amount of X-ray dose to be used during imaging, an exposure time to be used during imaging, a collimation area, and an imaging frame rate to be used during fluoroscopic imaging, and so forth. More generally, the operator may set a value of an image acquisition parameter of an imaging system that is used in the procedure. Another example of a parameter of the medical equipment that may be set by an operator in this example procedure relates to the patient table. An operator may set a value of a parameter of the patient table in order to control a position of the patient table and to thereby position the patient during the medical procedure. The parameter of the patient table may control a height, or a longitudinal position, of the patient table, for example. Another example of a parameter of the medical equipment that may be set by an operator in this example procedure relates to the contrast agent injector. An operator may set a value of a parameter of the contrast agent injector in order to provide a contrast agent-enhanced image of the region of interest in the patient during the medical procedure. The parameter of the contrast agent injector may control a factor such as an injection rate of the contrast agent, a total amount of injected contrast agent, a type of the contrast agent that is injected, a timing of the start, a timing of the end, and a duration, of the contrast agent injection, for example. In other types of medical procedures, other types of medical equipment may be used. For instance, other procedures may use medical imaging equipment such as a respirator, a defibrillator, a robotic device controller or manipulator, an aspiration device for removing blood clots, a laser (atherectomy, or optical position determination) device, and so forth. In such procedures, the operator may similarly set the values of parameters of the equipment in order to control the equipment.

Another type of interaction that may be performed by an operator during a medical procedure involving medical equipment is to set a value of an image visualization parameter for an image generated by the medical equipment through the user interface device With reference to the coronary angiography procedure describe above, one example of an image visualization parameter of the medical equipment that may be set by an operator in this example procedure relates to the X-ray imaging system. In this example, an operator may set a value of an image visualization parameter of the X-ray imaging system in order to control the display of X-ray images that are used to guide the procedure. The image visualization parameter may control a factor such as a magnification of a displayed X-ray image, or a mapping of pixel intensity values in the displayed X-ray image. For instance, the parameter may control a zoom level of the displayed image, or it may control a mapping function that is used to convert X-ray attenuation values to displayed pixel intensity values. In other types of medical procedures, other types of medical imaging equipment may be used. For instance, other procedures may use a CT imaging system, a PET imaging system, a SPECT imaging system, an ultrasound imaging system, an IVUS imaging system, an OCT imaging system, and so forth. In such procedures, the operator may similarly set the values of image visualization parameters for images that are generated by the medical imaging equipment.

In general, the operator interaction data 150 that is received in the operation S110 is generated by a user interface device associated with the medical equipment. For instance, in the example of a catheter/guidewire manipulator, a user may interact with various switches, buttons, or a touch screen of a user interface device in order to control a position the catheter/guidewire in the vasculature. In response to the operator's interactions, the user interface device generates the operator interaction data 150. A user interface device may similarly be used to control other types of medical equipment, including for example an X-ray imaging system, an ultrasound imaging system, an IVUS imaging system, a patient table, a contrast agent injector, and so forth. In some examples, the user interface device may be dedicated to the medical equipment, whereas other examples, the user interface device may be shared with other equipment. For instance, the user interface device of a contrast agent injector may include various buttons that are dedicated to the contrast agent injector, whereas, the user interface device of an imaging system may be provided by touchscreen, or a keyboard, or a mouse, and which is shared by other equipment.

The operator interaction data 150 that is generated by the user interface device may be recorded in a log file. In some examples, the operator interaction data 150 may be record in a log file of the user interface device. For instance, user interface devices such as a keyboard, or a touchscreen, or a mouse may have a dedicated log file that records operator interaction data that is generated in response to the operator's interactions. In other examples, the operator interaction data 150 may be record in a log file of the medical equipment. For instance, medical imaging equipment, such as an X-ray imaging system, typically generates a log file that includes the values of parameters that represent its status. This log file typically includes the values of image acquisition parameters that are used during imaging.

In the operation S110 described above with reference to FIG. 1, the operator interaction data may therefore be received from a log file associated with the medical equipment. The operator interaction data 150 may in general be received via any form of data communication, including wired, optical, and wireless communication. By way of some examples, when wired or optical communication is used, the communication may take place via signals transmitted on an electrical or optical cable, and when wireless communication is used, the communication may for example be via RF or optical signals. With reference to the example system illustrated in FIG. 2, the operator interaction data 150 may be received from the medical equipment, i.e. from the X-ray imaging system 110, or from the contrast agent injector 120, or from the patient table 130. In the example illustrated in FIG. 2, the operator interaction data 150 is received by one or more processors 310.

Returning to the method illustrated in FIG. 1, in the operation S120, the received operator interaction data 150 is inputted into a neural network 170. The neural network 170 is trained to generate a latent space encoding 180 of the operator interaction data. Various examples of neural networks that may be used for this purpose are described below with reference to FIG. 3-FIG. 6.

In general, the neural network 170 may be implemented by one or more processors. The one or more processors may be provided by the one or more processors 310 illustrated in FIG. 2, for example. The one or more processors may be disposed in various locations. For example, the neural network may be implemented by one or more processors that are local to the medical equipment. Alternatively, the neural network may be implemented by one or more processors that are disposed in a remote location. For example, the neural network may be implemented by one or more processors that are provided by a server, or it may be implemented by a distributed processing arrangement such as the Cloud, for example.

Figure 3:
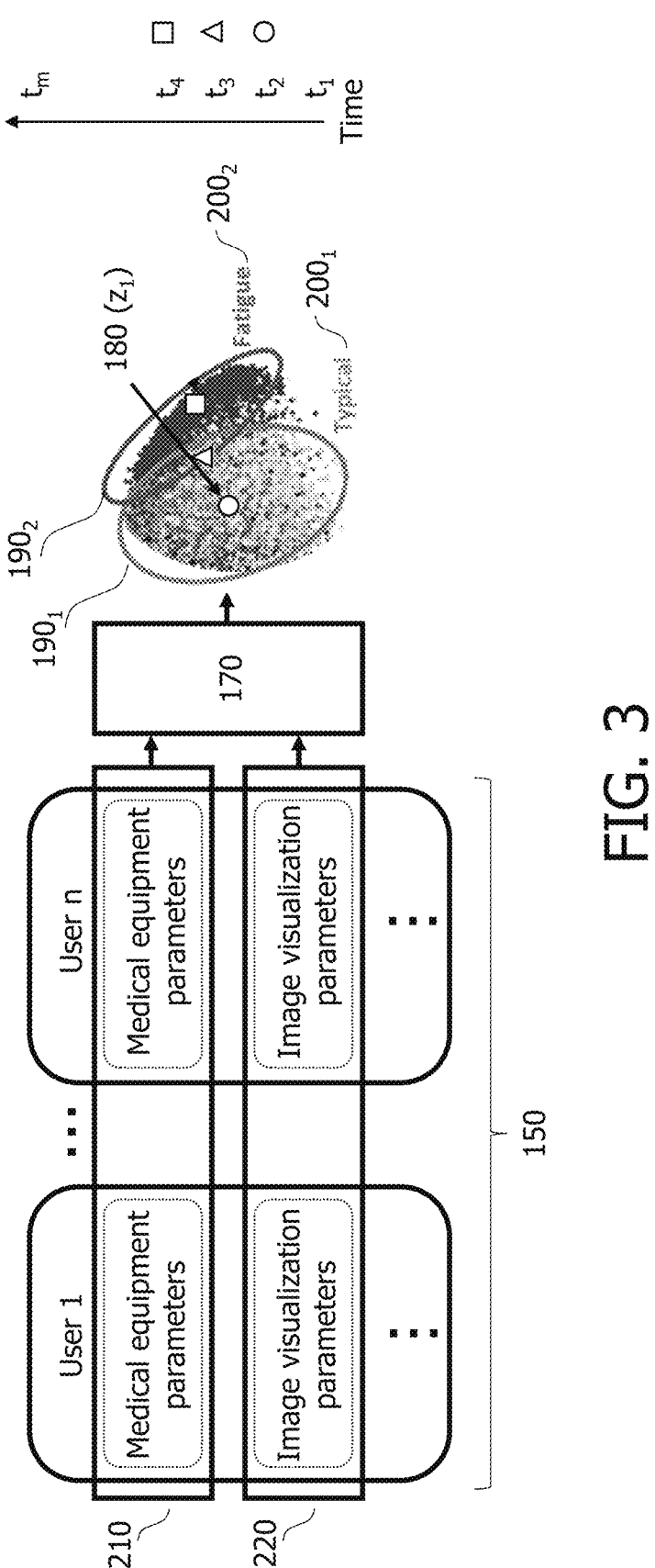
FIG. 3 is a schematic diagram illustrating an example of a neural network 170 that is trained to generate a latent space encoding of operator interaction data 150, in accordance with some aspects of the present disclosure.

FIG. 3 is a schematic diagram illustrating an example of a neural network 170 that is trained to generate a latent space encoding of operator interaction data 150, in accordance with some aspects of the present disclosure. The neural network 170 illustrated in FIG. 3 may be provided by various types of architectures. In general, generative models such as a variational autoencoder "VAE" may be used. In examples in which the operator interaction data 150 may be represented by an independent variable, the neural network may have a convolutional neural network "CNN" architecture. For instance, parameters of the medical equipment such as an X-ray dose, and an orientation of an X-ray imaging system, may be represented by an independent variable. In these examples the neural network may therefore have a CNN architecture. In examples in which the operator interaction data 150 represents a sequence of operator interactions, the neural network may have a temporal convolutional network "TCN" architecture, or a recurrent neural network "RNN" architecture, or a transformer architecture. For instance, the operator interaction data 150 may represent a sequence of instructions to control a catheter/guidewire manipulator in order to control a position of the catheter/guidewire in the vasculature. In these examples the neural network may therefore have a TCN architecture, or a RNN architecture, or a transformer architecture.

As mentioned above, in the operation S120, the operator interaction data 150 is inputted into the neural network 170. This operation is illustrated on the left-hand side of the example illustrated in FIG. 3. In the illustrated example, the operator interaction data 150 includes parameters of the medical equipment 210, and image visualization parameters 220. In this example, the operator interaction data 150 is provided by multiple, i.e. n, users, and there are two different types of operator interaction data 150. More generally, there may be one or more users, and there may be one or more different types of operator interaction data 150. The operator interaction data 150 may be generated in response to the various types of operator interactions described above.

In response to the inputting of the operator interaction data 150 into the neural network 170, the neural network 170 generates a latent space encoding 180 of the operator interaction data 150. The latent space encoding may be represented by a point in space. An example of a latent space encoding 180, $z_1$, is illustrated as a circle symbol on the right-hand side of FIG. 3.

The neural network 170 illustrated in FIG. 3 is trained to generate a latent space encoding of the operator interaction data 150. The neural network is trained to generate the latent space encoding by a training process that involves inputting into the neural network 170, training data representing a plurality of sets of operator interactions with the medical equipment.

The neural network 170, 230 is trained to generate the latent space encoding of the operator interaction data 150, by:

receiving training data representing a plurality of sets of operator interactions with the medical equipment;

inputting the training data into the neural network 170, 230; and for each of a plurality of the sets of operator interactions:

generating a latent space encoding z, 180, 240 of the inputted training data, using the neural network 170, 230;

reconstructing the inputted training data from the latent space encoding z, 180, 240, using the neural network 170, 230; and adjusting parameters of the neural network 170, 230 based on a difference between the inputted training data and the reconstructed inputted training data; and repeating the generating, the reconstructing, and the adjusting, until a stopping criterion is met.

As mentioned above, the neural network 170 illustrated in FIG. 3 may be provided by a VAE architecture. A VAE includes an encoder, and a decoder. During training, both the encoder and decoder are trained by adjusting the values of their parameters using training data. The training data represents a plurality of sets of operator interactions with the medical equipment. However, at inference, only the encoder portion is required. During the training of the VAE, for each set of operator interactions in the training data that are inputted into the neural network 170, the encoder generates a latent space encoding, 180, $z_1$, that represents the operator interactions. The decoder (not illustrated in FIG. 3) is forced to reconstruct the inputted training data from the latent space encoding 180, $z_1$ that is generated by the encoder. As described in more detail below, during training, a technique known as backpropagation is used to adjust the parameters of the neural network so as to minimize the difference between the inputted training data, and the reconstructed training data that is provided by the decoder. During training, the parameters of the encoder and the decoder, are adjusted based on the value of a loss function. The value of the loss function represents the difference between the inputted training data, and the reconstructed training data. Loss functions such as the L1 norm, the L2 norm, and so forth may be used for this purpose. Loss functions may also be used that force the learned distributions to be similar to a reference distribution. For example, the values of loss functions such as the Kullback Leibler "KL" divergence, may be used for this purpose, and which use a standard gaussian distribution as the reference distribution.

The training of a neural network involves inputting a training dataset into the neural network, and iteratively adjusting the neural network's parameters until the trained neural network provides an accurate output. Training is often performed using a Graphics Processing Unit "GPU" or a dedicated neural processor such as a Neural Processing Unit "NPU" or a Tensor Processing Unit "TPU". Training often employs a centralized approach wherein cloud-based or mainframe-based neural processors are used to train a neural network. Following its training with the training dataset, the trained neural network may be deployed to a device for analyzing new input data during inference. The processing requirements during inference are significantly less than those required during training, allowing the neural network to be deployed to a variety of systems such as laptop computers, tablets, mobile phones and so forth. Inference may for example be performed by a Central Processing Unit "CPU", a GPU, an NPU, a TPU, on a server, or in the cloud.

The process of training the neural network 170 described above therefore includes adjusting its parameters. The parameters, or more particularly the weights and biases, control the operation of activation functions in the neural network. In supervised learning, the training process automatically adjusts the weights and the biases, such that when presented with the input data, the neural network accurately provides the corresponding expected output data. In order to do this, the value of the loss functions, or errors, are computed based on a difference between predicted output data and the expected output data. The value of the loss function may be computed using functions such as the negative log-likelihood loss, the mean absolute error (or L1 norm), the mean squared error, the root mean squared error (or L2 norm), the Huber loss, or the (binary) cross entropy loss. Other loss functions like the Kullback-Leibler divergence may additionally be used when training a variational autoencoder to ensure that the distribution(s) $190_1$, $190_2$ of latent space encodings generated from the latent interaction data 150 is similar to a standard Gaussian distribution with mean 0 and standard deviation of 1. During training, the value of the loss function is typically minimized, and training is terminated when the value of the loss function satisfies a stopping criterion. Sometimes, training is terminated when the value of the loss function satisfies one or more of multiple criteria.

Various methods are known for solving the loss minimization problem such as gradient descent, Quasi-Newton methods, and so forth. Various algorithms have been developed to implement these methods and their variants including but not limited to Stochastic Gradient Descent "SGD", batch gradient descent, mini-batch gradient descent, Gauss-Newton, Levenberg Marquardt, Momentum, Adam, Nadam, Adagrad, Adadelta, RMSProp, and Adamax "optimizers". These algorithms compute the derivative of the loss function with respect to the model parameters using the chain rule. This process is called backpropagation since derivatives are computed starting at the last layer or output layer, moving toward the first layer or input layer. These derivatives inform the algorithm how the model parameters must be adjusted in order to minimize the error function. That is, adjustments to model parameters are made starting from the output layer and working backwards in the network until the input layer is reached. In a first training iteration, the initial weights and biases are often randomized. The neural network then predicts the output data, which is likewise, random. Backpropagation is then used to adjust the weights and the biases. The training process is performed iteratively by making adjustments to the weights and biases in each iteration. Training is terminated when the error, or difference between the predicted output data and the expected output data, is within an acceptable range for the training data, or for some validation data. Subsequently the neural network may be deployed, and the trained neural network makes predictions on new input data using the trained values of its parameters. If the training process was successful, the trained neural network accurately predicts the expected output data from the new input data.

As mentioned above, the training of the neural network 170 involves inputting into the neural network 170, training data representing a plurality of sets of operator interactions with the medical equipment. In this respect, the training data may include some tens, or hundreds, or thousands, or more, of sets of interactions, and each set of interactions may include some tens, or hundreds, or thousands, of more, of interactions during the medical procedure.

The training data that is used to train the neural network 170 represents operator interactions with the medical equipment for one or more known characteristics of the operator behavior. In this regard, the known characteristics $200_1$, $200_2$ may include characteristics such as "target behavior", "typical behavior", "fatigued behavior", "inexperience", and "unexpected behavior", for example.

In some examples, the known characteristics of the operator behavior for the training data are assigned to the training data based on a manual assessment of the procedure from which the training data is generated. For instance, an observer may monitor the performance of the operators during the medical procedure and manually assign behavior labels such as "target behavior", "typical behavior", "fatigued behavior", "inexperience", and "unexpected behavior", to the operator interaction data.

Alternatively, the characteristics of the operator behavior for the training data may be assigned to the training data based on performance data. By way of some examples, the performance data may represent one or more of the following factors for a set of operator interactions: a duration of the medical procedure, a familiarity of the operator with the medical procedure, a familiarity of the operator with the medical equipment, a time of performing the medical procedure, and a workload of the operator. For instance, the duration of a medical procedure may be used to label a procedure with a relatively short duration as "Typical" or "Target behavior". By contrast, a procedure with a relatively longer duration may be labelled as "Fatigued" behavior. In this case, the training data includes performance data for each of a plurality of sets of operator interactions, and in the method described with reference to FIG. 1, the known characteristic $200_1$, $200_2$ of the operator behavior are assigned to the latent space encodings of the training data based on the performance data for the corresponding set of interactions.

Multiple different factors of the performance data may also be used to assign the known characteristic $200_1$, $200_2$ of the operator behavior to the training data. For instance, the duration of the procedure may be used in the context of a familiarity of the operator with the medical procedure, a time of performing the medical procedure, and a workload of the operator to adjust the characteristic that is assigned. For instance, the familiarity of the operator with the medical procedure may be used to re-label a procedure that is deemed to represent "Fatigued" behavior based on its relatively long duration, as "Typical" in the event that the operator is familiar with the procedure and the procedure is simply long due to its complexity.

The performance data may also be used to manually assess the procedure from which the training data is generated. For instance, the performance data may be used to re-label a procedure that is deemed "Typical" behavior by a manual assessor as "unexpected behavior" due to its long duration, or due to it being performed at an irregular time of the data. The performance data may similarly be used to explain latent space encodings of the training data that appear as outliers to the learned distribution. For instance, the performance data may be used to explain outliers as being a consequence of the medical procedure being performed at an irregular time of day, or as part of an emergency response, or with an operator that is unfamiliar with the medical equipment, or with an operator that has an unusually high workload.

During its training, the neural network 170 also learns a distribution of the latent space encodings of the sets of operator interactions that are used to train the neural network. The distribution(s) are learnt such that they correspond to the known characteristic(s) of the operator behavior for the training data. With reference to the example illustrated in FIG. 3, distributions $190_1$, $190_2$ of latent space encodings that have been learnt for the characteristics of "typical behavior" $200_1$, and "fatigued behavior" $200_2$, and which characteristics have been manually assigned to the training data in the manner described above. These distributions indicate the spread of latent space encodings for each of the known characteristics of the operator interaction data that is used to train the neural network. At inference, the learnt distribution(s) are used to determine characteristics of operator behavior for new sets of operator interactions with the medical equipment.

With reference to the method illustrated in FIG. 1, in the operation S130, a characteristic of the operator behavior is outputted based on a position of the latent space encoding 180 of the operator interaction data generated by the neural network 170, with respect to a distribution $190_1$, $190_2$ of latent space encodings of training data representing operator interactions with the medical equipment having known characteristics $200_1$, $200_2$ of the operator behavior.

In the operation S130, the position of the latent space encoding 180 may be determined with respect to a distribution $190_1$, $190_2$ of latent space encodings of the training data using various techniques.

In one example technique, it is determined whether the latent space encoding is within a distribution $190_1$, $190_2$ of latent space encodings of the training data. For instance, in the example illustrated in FIG. 3, the distributions of latent space encodings $190_1$, and $190_2$ have been learnt for the characteristics "Typical" $200_1$, and "Fatigue" $200_2$. The latent space encoding 180 that is indicated by the circle symbol is within the distribution $190_1$ for the known characteristic "Typical" behavior $200_1$. Consequently, using this example technique, in the operation S130, the characteristic "Typical" behavior is outputted.

In another example technique, the position of the latent space encoding 180 is determined with respect to a distribution $190_1$, $190_2$ of latent space encodings of training data by calculating a distance between the position of the latent space encoding 180 and a centroid of the distribution. This distance can be calculated using a function such as the Euclidean distance or the geodesic distance, for example. This distance provides an analogue measure of the proximity of the behavior characteristic for the inputted operator interaction data 150 to the known characteristic of the operator behavior. This measure may be represented, and also outputted, on a continuous scale as a fraction or percent representing how close the characteristic of the operator behavior represented by the operator interaction data is to the known characteristics $200_1$, $200_2$ of the operator behavior.

In examples in which a distribution of latent space encodings has been learnt for a multiple characteristics of the operator behavior, the operation S130 may involve calculating a value of a distance between the position of the latent space encoding 180 and a centroid of each of the learned distributions. In this case, the characteristic associated with the distribution having a centroid with the shortest distance is outputted. This is useful in discerning between the characteristics of operator behavior that have overlapping distributions. For example, this may be used to accurately assign a characteristic of the operator behavior to a latent space encoding represented by the triangular symbol in FIG. 3, and which is located within the overlap region between the distributions for the characteristics "Typical" behavior and "Fatigue" behavior.

In another example technique, the position of the latent space encoding 180 is determined with respect to a distribution $190_1$, $190_2$ of latent space encodings of training data by calculating within a predetermined radius around the position of the latent space encoding 180 the number of encodings of training data representing operator interactions with the medical equipment having known characteristics $200_1$, $200_2$ of the operator behavior. This may also be useful in discerning between characteristics of operator behavior that have overlapping distributions. For example, this may be used to accurately assign a characteristic of the operator behavior to a latent space encoding represented by the triangular symbol in FIG. 3 by evaluating within a neighborhood of the triangular symbol, the number of encodings of training data representing "Typical" behavior and "Fatigue" behavior. For instance, despite being equally close to the centroids of the distributions representing "Typical" behavior and "Fatigue" behavior, the percentage of encodings of training data representing "Typical" behavior within a neighborhood of the triangular symbol may be 70% and the percentage representing "Fatigue" behavior may be 30%, allowing "Typical" behavior to be assigned as the characteristic of the operator behavior at the triangular symbol. However, if the percentage of encodings representing "Typical" behavior was 53% and "Fatigue" behavior 47%, this allows the system to inform users of its uncertainty in assigning a characteristic of the operator behavior.

In one example, a clustering operation may be performed on the latent space encodings of the training data in order to provide a distribution $190_1$, $190_2$ of latent space encodings for each of one or more known characteristics $200_1$, $200_2$ of the operator behavior. In this example, in the method described with reference to FIG. 1, the latent space encodings of the training data are clustered to provide a distribution $190_1$, $190_2$ of latent space encodings for each of one or more known characteristics $200_1$, $200_2$ of the operator behavior. In this example, the operation of outputting S130 a characteristic of the operator behavior based on a position of the latent space encoding 180 of the operator interaction data generated by the neural network 170, with respect to a distribution $190_1$, $190_2$ of latent space encodings of training data representing operator interactions with the medical equipment having known characteristics $200_1$, $200_2$ of the operator behavior, comprises:

determining a distance between the latent space encoding 180 of the inputted operator interaction data 150 and a centroid of the distribution $190_1$, $190_2$ of the latent space encodings for each of the one or more known characteristics $200_1$, $200_2$ of the operator behavior; and outputting, as the characteristic of the operator behavior, the characteristic $200_1$, $200_2$ of the operator behavior for the distribution $190_1$, $190_2$ having a centroid with the shortest distance from the latent space encoding 180 for the inputted operator interaction data 150.

With reference to FIG. 3, in this example, the distances between the position of the latent space encoding 180 and a centroid of each of the distributions $190_1$, and $190_2$, are calculated. Since, in the example represented by the circular symbol, the shortest distance occurs for the distribution $190_1$, the characteristic "Typical" $200_1$ would be outputted in the operation S130. In another example, represented by the square symbol representing a later time in a medical procedure, the shortest distance occurs for the distribution $190_2$, the characteristic "Fatigue" $200_2$ would be outputted in the operation S130.

The operation of outputting S130 a characteristic of the operator behavior may be performed in various ways. In some examples, a characteristic of the operator behavior is outputted graphically. For example, the characteristic may be outputted graphically on a display device such as the monitor 140 illustrated in FIG. 2. The characteristic may be outputted as text, or as an icon, for example. For instance, the text "Typical behavior" may be outputted. Alternatively, the characteristic of the operator behavior may be outputted audially. For instance, a sound, or a sound message may be outputted that corresponds to the words "Typical behavior", or "Fatigued behavior". Alternatively, the characteristic of the operator behavior may be outputted via of a color of a lamp. For instance, a green lamp may be illuminated in the event of "Typical" behavior, and a red lamp may be illuminated in the event of "Fatigued" behavior.

In one example, a position of the latent space encoding is outputted graphically, and with respect to a distribution $190_1$, $190_2$ of latent space encodings generated from the training data. In this example, the method described with reference to FIG. 1 includes:

outputting a graphical representation of the position of the latent space encoding 180 of the operator interaction data 150, with respect to the distribution $190_1$, $190_2$ of latent space encodings generated from training data representing operator interactions with the medical equipment having known characteristics $200_1$, $200_2$ of the operator behavior.

In this example, the graphical representation may depict the distribution(s) $190_1$, $190_2$ for the training data as well as the latent space encoding for the inputted operator interaction data 150. This graphical representation may be provided in a similar manner to that illustrated on the right-hand side of FIG. 3, for example.

In one example, a confidence value is calculated for the latent space encoding, and the confidence value is outputted. The confidence value may be calculated using various techniques. For example, the neural network 170 may calculate the confidence value using the dropout technique. The dropout technique involves iteratively inputting the same data into the neural network 170 and determining the neural network's output whilst randomly excluding a proportion of the neurons from the neural network in each iteration. The outputs of the neural network are then analyzed to provide mean and variance values. The mean value represents the final output, and the magnitude of the variance indicates whether the neural network is consistent in its predictions, in which case the variance is small and the confidence value is relatively higher, or whether the neural network was inconsistent in its predictions, in which case the variance is larger and the confidence value is relatively lower. The confidence may alternatively be calculated using e.g. the Kullback-Leibler "KL" divergence, between the distribution that the latent space encoding 180 is sampled from, and the distribution over the current trained encodings. This divergence indicates how well the input sequence is represented by the learned encodings. A low value of confidence may indicate that the trained neural network 170 is not suitable for processing the inputted operator interaction data 150. For example, the input data may be out-of-distribution as compared to the data that was used to train the neural network.

In another example, a warning is outputted based on the outputted characteristic of the operator behavior. For instance, a warning may be outputted if the characteristic of the operator behavior that is outputted in the operation S130 represents a risk to the safety of a patient. The warning may be outputted using the techniques described above, i.e. graphically, audially, or via of a color of a lamp.

In one example, the neural network 170 generates a latent space encoding for operator interaction data 150 that is generated over each of multiple time intervals. In this example, the operations of receiving S110 operator interaction data 150, inputting S120 the operator interaction data 150 into a neural network 170, and outputting S130 a characteristic of the operator behavior, and which were described above with reference to FIG. 1, are performed for operator interaction data 150 that is generated over a plurality of different time intervals $t_1$-$t_2$, $t_2$-$t_3$, $t_3$-$t_4$.

With reference to FIG. 3, in this example, operator interaction data may be inputted into the neural network for each of the time intervals $t_1$-$t_2$, $t_2$-$t_3$, and $t_3$-$t_4$. In response, the neural network 170 generates latent space encodings for the operator interaction data 150 for each of these time intervals. For each time interval, the position of the latent space encoding that is generated by the neural network, is determined with respect to a distribution $190_1$, $190_2$ of latent space encodings of training data representing operator interactions with the medical equipment having known characteristics $200_1$, $200_2$ of the operator behavior. Thus, the position of the latent space encodings for each of the time intervals are determined with respect to the distributions $190_1$, and $190_2$ illustrated in FIG. 3. As illustrated by the circle, triangle, and square symbols that corresponds to each of these time intervals, over time, the latent space encoding for the inputted operator interaction data moves from within the distribution $190_1$ for the characteristic "Typical" behavior $200_1$, towards, and ultimately into, the distribution $190_2$ for the characteristic "Fatigue" behavior $200_2$. In this example, the characteristic "Typical" behavior $200_1$, would be outputted for the time intervals $t_1$-$t_2$ and $t_2$-$t_3$, and the characteristic "Fatigue" behavior $200_2$ would be outputted for the time interval $t_3$-$t_4$. In this example, the method therefore outputs a characteristic of the operator behavior that is updated over time. This information may be used inter alia to alert a physician of the need to assign an additional operator to the current medical procedure in order to share the workload. The time intervals illustrated in FIG. 3 may correspond to fixed time intervals, such as a fixed number of seconds, minutes, or hours, or they may correspond to different phases of the medical procedure. For example, with reference to the example balloon angioplasty procedure described above, the time intervals may be selected so as to correspond to each of a catheterization phase, a balloon insertion phase, a balloon expansion phase, and a procedure verification phase. The time intervals may also be selected in other ways, for instance, a first time interval may correspond to the period $t_1$-$t_2$, and a second time interval may correspond to a period $t_1$-$t_3$, and a third time interval may correspond to a period $t_1$-$t_4$. In so doing, the characteristic of the operator behavior may be outputted based on all operator interaction data 150 that is generated since a common point in time in the procedure, i.e. $t_1$.

In one example, the method described with reference to FIG. 1 includes:

receiving medical equipment identification data representing a type of the medical equipment used during the medical procedure; and wherein the outputting S130 a characteristic of the operator behavior is based further on the received medical equipment identification data.

The medical equipment identification data may be provided for various types of medical equipment, including imaging equipment, a contrast agent injector, a ventilator, a defibrillator, and so forth. The medical equipment identification data may also be provided for other medical equipment that is used in the procedure, such as a catheter, a stent, a guidewire, for example. The medical equipment identification data may be used in various ways. For instance, the neural network may be trained to generate the latent space encoding of the operator interaction data based further on the inputted medical equipment identification data. In this case, the medical equipment identification data is used as an input to the neural network during training, and is also provided as an input to the neural network at inference. At inference, the medical equipment identification data for the medical procedure is inputted into the neural network, and this data is used to generate the latent space encodings of the operator interaction data. Alternatively, the medical equipment identification data may be used to select a neural network for use in the method that is trained using corresponding medical equipment identification data. Alternatively, the medical equipment identification data may be used to label the latent space encodings of the training data. In this case, when outputting S130 a characteristic of the operator behavior based on a position of the latent space encoding 180 of the operator interaction data generated by the neural network 170, the position may be determined with respect to a distribution $190_1$, $190_2$ of latent space encodings of training data representing operator interactions with the medical equipment having known characteristics $200_1$, $200_2$ of the operator behavior that has corresponding medical equipment identification data.

In one example, the neural network 170 is trained to generate the latent space encoding 180 of the operator interaction data 150 based further on peripheral hardware data generated during the medical procedure. In this example the method described with reference to FIG. 1 includes:

receiving peripheral hardware data generated during the medical procedure;

inputting the peripheral hardware data into the neural network 170; and wherein the outputting S130 a characteristic of the operator behavior based on a position of the latent space encoding 180 of the operator interaction data generated by the neural network 170, is based further on the inputted peripheral hardware data.

In this example, the peripheral hardware may include hardware such as a camera configured to record the medical procedure, a microphone configured to record sounds generated during the medical procedure, and so forth. In this example, the neural network 170 illustrated in FIG. 3 is trained to generate the latent space encoding of the operator interaction data based further on the inputted medical equipment identification data. In this case, the medical equipment identification data is used as an input to the neural network during training, and also at inference. At inference, the medical equipment identification data for the medical procedure is inputted into the neural, and this data is used to generate the latent space encodings of the operator interaction data. The peripheral hardware data for peripheral devices such as a camera, a microphone, and so forth, augments the operator interaction data during both the training of the neural network, and also in the generation of predictions by the neural network at inference. Peripheral hardware data from a camera may capture information relating to the positions and the movements of the operators during the medical procedure. The data may for example capture the movements of the physician's hands during the manipulation of a catheter or guidewire. Peripheral hardware data from a camera may capture information such as which side of a patient the physician is standing during a medical procedure. This information may correlate with the behavioral characteristics of the operators during the medical procedure, and can therefore fine-tune the latent space encodings that are generated by the neural network 170. Similarly, peripheral hardware data from a microphone includes information from the voices of the operators, and sounds generated by the medical equipment during the procedure. This information may correlate with the behavioral characteristics of the operators during the medical procedure, and can therefore also fine-tune the latent space encodings that are generated by the neural network 170.

The size, or dimension, of the operator interaction data 150 that is inputted into the neural network can vary depending on the type of interaction that it represents. For instance, the size of operator interaction data that represents interactions such as the setting of a value of a parameter of the medical equipment 110, 120, 130, 140 used during the medical procedure, may differ from the size of operator interaction data that represents interactions such as the setting of a value of an image visualization parameter for an image generated by the medical equipment. The different sizes of the operator interaction data 150 can be difficult to consolidate in a single neural network such as the neural network 170 illustrated in FIG. 3. Thus, in one example, a separate neural network is trained for each of multiple types of interaction 210 with the medical equipment. This example is described with reference to FIG. 4, which is a schematic diagram illustrating a first example of a neural network 170 that is trained to generate a latent space encoding of operator interaction data 150 representing a first type of interaction 210 with the medical equipment, and a second neural network 230 that is trained to generate a latent space encoding of operator interaction data 150 representing a second type of interaction 220 with the medical equipment, in accordance with some aspects of the present disclosure. In this example, the received operator interaction data 150 represents a first type of interaction 210 selected from the group: setting a value of a parameter of the medical equipment used during the medical procedure, and setting a value of an image visualization parameter for an image generated by the medical equipment, and the neural network 170 is trained to generate a latent space encoding 180 of the operator interaction data for the first type of interaction 210. The method described with reference to FIG. 1 includes:

receiving operator interaction data representing a second type of interaction 220 selected from the group: setting a value of a parameter of the medical equipment used during the medical procedure, and setting a value of an image visualization parameter for an image generated by the medical equipment, the second type of interaction 220 being different to the first type of interaction 210; inputting the operator interaction data representing the second type of interaction 220 into a second neural network 230, the second neural network being trained to generate a latent space encoding 240 of the operator interaction data for the second type of interaction 220; and wherein the outputting S130 a characteristic of the operator behavior is based on:

the position of the latent space encoding 180 of the operator interaction data for the first type of interaction 210 generated by the neural network 170, with respect to the distribution $190_1$, $190_2$ of latent space encodings generated from training data representing operator interactions for the first type of interaction 210 with the medical equipment having known characteristics $200_1$, $200_2$ of the operator behavior; and the position of the latent space encoding 240 of the operator interaction data for the second type of interaction 220 generated by the second neural network 230, with respect to the distribution $250_1$, $250_2$ of latent space encodings generated from training data representing operator interactions for the second type of interaction with the medical equipment having known characteristics $260_1$, $260_2$ of the operator behavior.

In this example, a first neural network 170 is trained to generate latent space encodings of operator interaction data for a first type of interaction 210 with the medical equipment, and a second neural network 230 is trained to generate latent space encodings of the operator interaction data for a second type of interaction 220. Each neural network is trained in the same manner as described above, and using operator interaction data for the respective type of interaction 210, 220. At inference, a separate latent space encoding is generated for each type of interaction 210, 220. The operations of determining the positions of the latent space encodings 180, 240 of the operator interaction data for each type of interaction 210, 220 with respect to the distributions of latent space encodings generated from training data, are determined for each of the neural networks 170, 230 in the same manner as described above.

Figure 4:
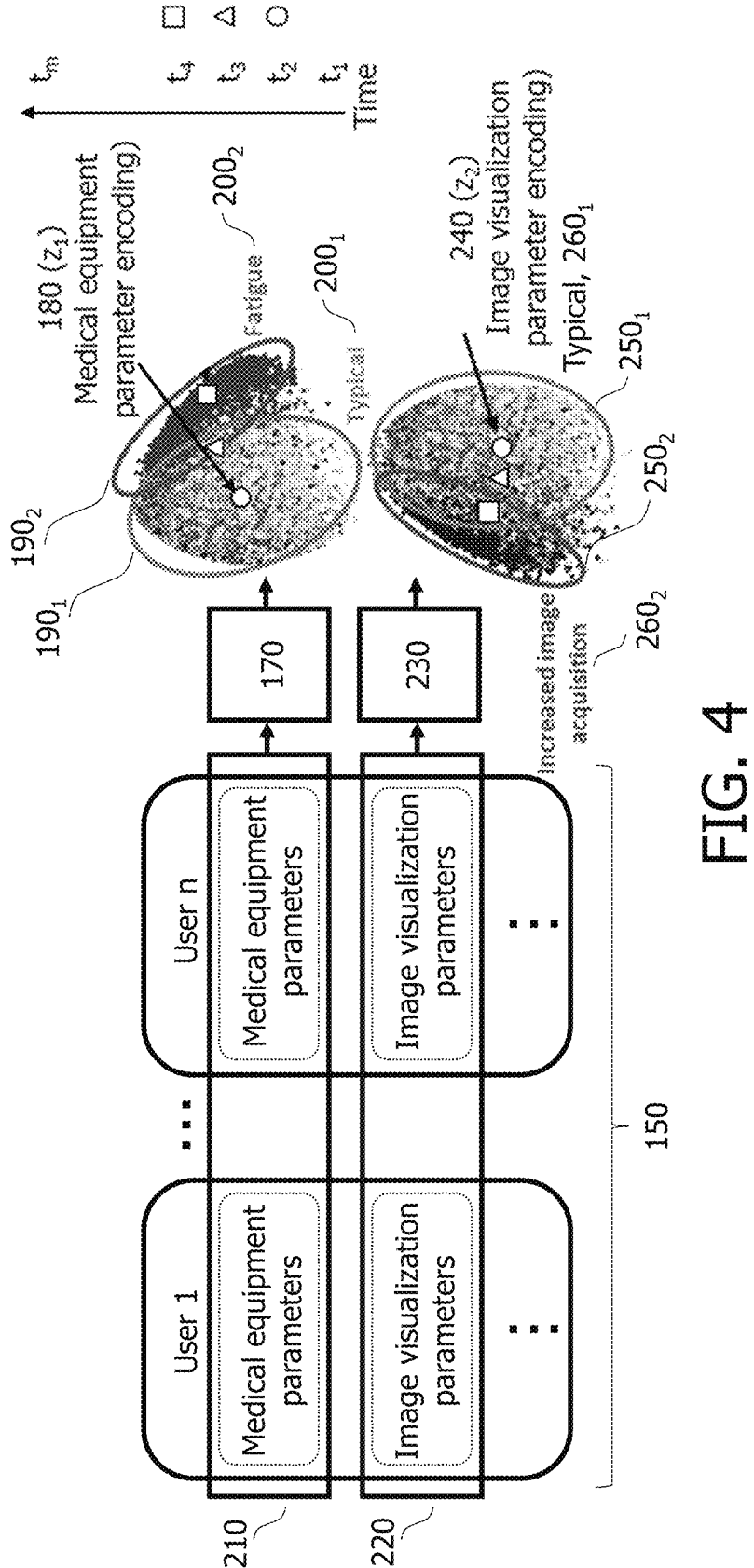
FIG. 4 is a schematic diagram illustrating a first example of a neural network 170 that is trained to generate a latent space encoding of operator interaction data 150 representing a first type of interaction 210 with the medical equipment, and a second neural network 230 that is trained to generate a latent space encoding of operator interaction data 150 representing a second type of interaction 220 with the medical equipment, in accordance with some aspects of the present disclosure.

The distributions with respect to which the positions of the latent space encodings are determined, may have the same characteristics of the operator behavior, or they may have different characteristics. For example, with reference to FIG. 4, both the distributions $190_1$ and $250_1$ are provided for the same characteristic of "Typical" behavior $200_1$, and $260_1$. The distributions $190_2$ and $250_2$ are provided for different characteristics, i.e. of "Fatigue" behavior $200_2$, and "Increased image acquisition" $260_2$. In some examples, the characteristic for each latent space encoding is outputted. This may be useful if the distributions 190 and 250 are provided for different characteristics. In some examples, the characteristics for the latent space encodings are combined. This may be useful if the distributions 190 and 250 are provided for the same characteristics. For example, if the latent space encodings that are generated for the interactions 210, 220 in FIG. 4 are both deemed to represent "Typical" behavior, a single characteristic of "Typical" behavior may be outputted in the operation S130.

Figure 5:
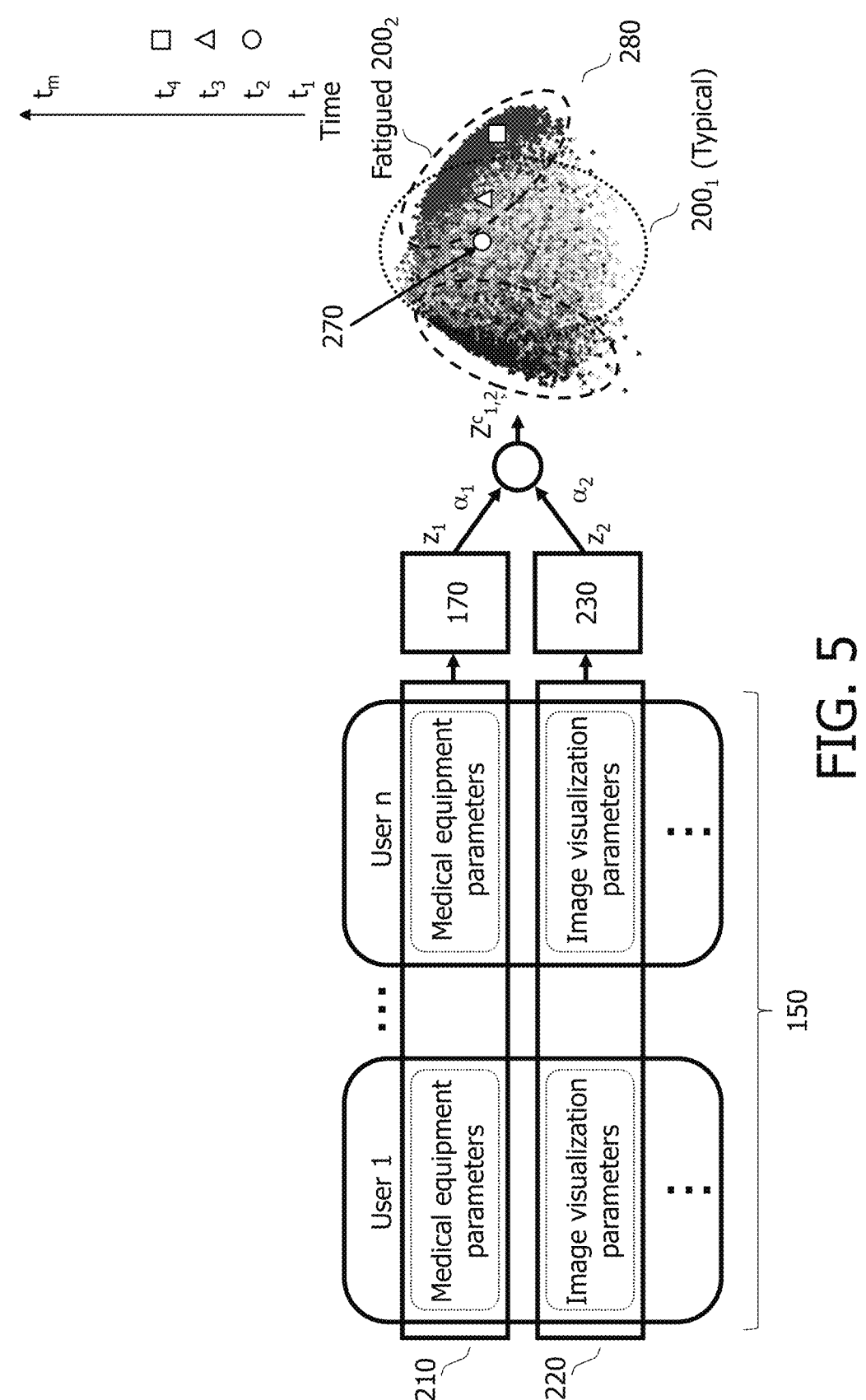
FIG. 5 is a schematic diagram illustrating a second example of a neural network 170 that is trained to generate a latent space encoding of operator interaction data 150 representing a first type of interaction 210 with the medical equipment, and a second neural network 230 that is trained to generate a latent space encoding of operator interaction data 150 representing a second type of interaction 220 with the medical equipment, in accordance with some aspects of the present disclosure.
Figure 6:
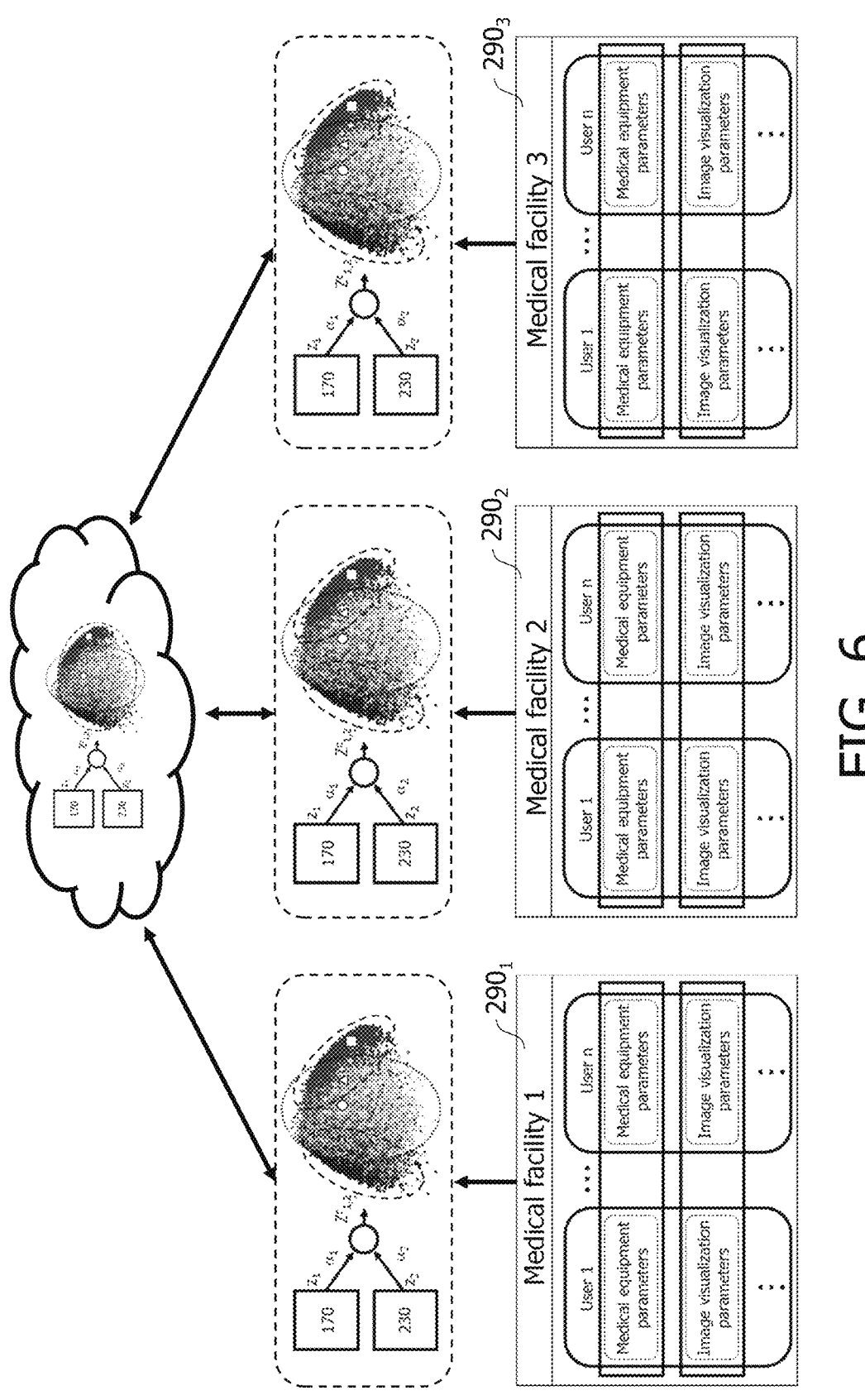
FIG. 6 is a schematic diagram illustrating an example of multiple neural networks 170, 230 that are trained using the training data for a plurality of different batches $290_{1 \ldots n}$ of one or more users, in accordance with some aspects of the present disclosure.

Another example in which a separate neural network is trained for each of multiple types of interaction 210 with the medical equipment is described with reference to FIG. 5. FIG. 5 is a schematic diagram illustrating a second example of a neural network 170 that is trained to generate a latent space encoding of operator interaction data 150 representing a first type of interaction 210 with the medical equipment, and a second neural network 230 that is trained to generate a latent space encoding of operator interaction data 150 representing a second type of interaction 220 with the medical equipment, in accordance with some aspects of the present disclosure. In this example, the received operator interaction data represents a first type of interaction 210 selected from the group: setting a value of a parameter of the medical equipment used during the medical procedure, and setting a value of an image visualization parameter for an image generated by the medical equipment, and the neural network 170 is trained to generate a latent space encoding 180 of the operator interaction data for the first type of interaction 210. In this example, the method described with reference to FIG. 1 includes:

receiving operator interaction data representing a second type of interaction 220 selected from the group: setting a value of a parameter of the medical equipment used during the medical procedure, and setting a value of an image visualization parameter for an image generated by the medical equipment, the second type of interaction 220 being different to the first type of interaction 210;

inputting the operator interaction data representing a second type of interaction 220 into a second neural network 230, the second neural network being trained to generate a latent space encoding of the operator interaction data for the second type of interaction 220; and wherein the outputting S230 a characteristic of the operator behavior is based on a position of a weighted latent space encoding 270 with respect to a weighted distribution 280 of latent space encodings generated from training data representing operator interactions including the first type of interaction 210 and the second type of interaction 220 with the medical equipment and having known characteristics of the operator behavior $200_1$, $200_2$, and wherein the weighted latent space encoding is determined by combining:

a weighting $a_1$ of the latent space encoding of the operator interaction data for the first type of interaction 210 generated by the neural network 170; and a weighting $a_2$ of the latent space encoding of the operator interaction data for the second type of interaction 220 generated by the second neural network 230.

In this example, a first neural network 170 is trained to generate latent space encodings $z_1$ of operator interaction data for a first type of interaction 210 with the medical equipment, and a second neural network 230 is trained to generate latent space encodings $z_2$ of the operator interaction data for a second type of interaction 220. Weightings $a_1$, and $a_2$ are applied to the latent space encodings $z_1$ and $z_2$ that are generated by each neural network. The values of the weightings $a_1$, and $a_2$ may be parameters of the neural network that are learned during training. The first neural network 170 and the second neural network 230 are trained together. The weightings $a_1$, and $a_2$ are applied to the latent space encodings that are generated by the first neural network 170 and the second neural network 230 to generate a combined latent space encoding $z^c_{1,2}$ for the inputted operator interaction data 150 for each of the first type of interaction 210 and the second type of interaction 220, respectively. The combined latent space encoding $z^c_{1,2}$ may be computed in various ways. For example the combined latent space encoding $z^c_{1,2}$ may be computed as a weighted sum, or the weighted vectors could be concatenated, and a non-linear operator applied. The combined latent space encodings $z^c_{1,2}$ that are learned during training form a single weighted distribution 280 of latent space encodings. At inference, a position of the combined latent space encoding $z^c_{1,2}$ for inputted operator interaction data 150, is determined with respect to the weighted distribution 280.

In this example, the neural network 170 and the second neural network 230 are trained to generate the latent space encoding of the operator interaction data 150, by:

receiving training data representing a plurality of sets of operator interactions with the medical equipment, the operator interactions representing the first type of interaction $210$ and the second type of interaction $220$;

inputting the training data representing the first type of interaction $210$ into the neural network $170$;

inputting the training data representing the second type of interaction $220$ into the second neural network $230$; and for each of a plurality of the sets of operator interactions:

generating a latent space encoding $z_1$ of the inputted training data representing the first type of interaction $210$, using the neural network $170$;

generating a latent space encoding $z_2$ of the inputted training data representing the second type of interaction $220$, using the second neural network $230$;

applying weightings $a_1$, $a_2$ to the latent space encodings $z_1$, $z_2$ of the operator interaction data generated by the neural network $170$ and the second neural network $230$ to provide a combined latent space encoding $z^c_{1,2}$ of the operator interaction data;

reconstructing the inputted training data representing the first type of interaction from the combined latent space encoding $z^c_{1,2}$, using the neural network $170$;

reconstructing the inputted training data representing the second type of interaction from the combined latent space encoding $z^c_{1,2}$, using the second neural network $230$; and adjusting the applied weightings $a_1$, $a_2$, and the parameters of the neural network $170$ and the second neural network $230$, based on a difference between the inputted training data and the reconstructed inputted training data for each of the neural network $170$ and the second neural network $230$; and repeating the generating, the reconstructing, and the adjusting, until a stopping criterion is met.

As mentioned above, in this example, the neural network $170$ and the second neural network $230$ are trained together. The values of the weightings $a_1$, and $a_2$ are parameters of the neural network that are learned during training. During training, a decoder portion of neural network (not illustrated in FIG. 5) is forced to reconstruct the inputted operator interaction data $150$ from the combined latent space encoding $z^c_{1,2}$ for each set of operator interactions. During training, the value of a loss function is calculated and used to adjust the parameters of the neural networks via backpropagation. The value of the loss function represents the difference between the inputted training data and the reconstructed inputted training data. Loss functions such as the L1 norm, the L2 norm, and so forth may be used for this purpose.

In one example, the training data that is used to train the neural networks illustrated in FIG. 3-FIG. 5 is provided for a group of users. A group of users may be defined as a selection of types of users that typically work together on a medical procedure, or a selection of specific users that typically work together on a medical procedure. For instance, a group of users may include a fellow, a nurse, a radiology technician, an anesthesiologist, and so forth. In this example, the neural network is trained with training data for the group of users. The training of the neural network with such data provides a distribution of latent space encodings of training data representing operator interactions with the medical equipment having known characteristics of the operator behavior for the group of users. In this example, the trained neural network is then used to perform inference with operator interaction data that is generated during medical procedures that are performed by the same group of users. The latent space encodings of the users is expected to be within the distribution for the group. If the group represents specific users, significant changes in the latent space encodings for a procedure, for example latent space encodings that fall outside the distribution for the group, may be used to identify procedures in which there has been a change in the behavior of the group over time. If the group represents types of users, this example may be used to trigger suggestions to the group that help replicate the dynamics of a higher performance team.

In this example, the training data represents a plurality of sets of operator interactions with the medical equipment for a group of users; and the method of assessing operator behavior during a medical procedure involving medical equipment comprises:

outputting S130 the characteristic of the operator behavior based on the position of the latent space encoding of the operator interaction data generated by the neural network, with respect to the distribution of latent space encodings of training data representing operator interactions with the medical equipment having known characteristics of the operator behavior for the group of users.

In one example, a federated learning setting is used wherein the values of the parameters of multiple separate neural networks are determined by training each neural network with training data for a separate batch of users. The parameters of the separate neural networks are then combined to provide parameters for a global neural network. The global neural network is then deployed to each batch of users to perform inference. In so doing, the global neural network benefits from the data diversity from the batches of users, some of which may have only a few users, or only a single user. The batches of users may come from various hospitals or medical sites, allowing the global neural network to benefit from the larger user base without requiring the various hospitals or medical site to share their data outside the respective hospitals or medical sites. This example also facilitates an analysis of user behavior without compromising user identity. This example is described with reference to FIG. 6, which is a schematic diagram illustrating an example of multiple neural networks $170$, $230$ that are trained using the training data for a plurality of different batches $290_{1 \ldots n}$ of one or more users, in accordance with some aspects of the present disclosure. This example may be used with the neural networks illustrated in FIG. 3-FIG. 5. In this example, the training data represents a plurality of sets of operator interactions with the medical equipment for a batch $290_{1 \ldots n}$ of one or more users; and the training of the neural network includes performing the inputting the training data into the neural network, and the repeating the generating, the reconstructing, and the adjusting, until a stopping criterion is met, using sets of operator interactions for each of a plurality of different batches $290_{1 \ldots n}$ of one or more users to provide a plurality of corresponding neural networks $170$, $230$, each neural network being trained using the training data for a different batch of users; and wherein the method of assessing operator behavior during a medical procedure involving medical equipment comprises performing the inputting S110 the operator interaction data $150$ into a neural network $170$, $230$ using a neural network having parameters that are determined based on a combination of the parameters from the neural networks $170$, $230$ trained using the training data for a plurality of different batches $290_{1 \ldots n}$ of one or more users.

In another example, a computer program product, is provided. The computer program product comprises instructions which when executed by one or more processors, cause the one or more processors to carry out a method of assessing operator behavior during a medical procedure involving medical equipment 110, 120, 130, 140. The method includes:

receiving S110 operator interaction data 150 representing operator interactions 160 with the medical equipment during the medical procedure;

inputting S120 the operator interaction data 150 into a neural network 170, the neural network being trained to generate a latent space encoding 180 of the operator interaction data; and outputting S130 a characteristic of the operator behavior based on a position of the latent space encoding 180 of the operator interaction data generated by the neural network 170, with respect to a distribution 190$_1$, 190$_2$ of latent space encodings of training data representing operator interactions with the medical equipment having known characteristics 200$_1$, 200$_2$ of the operator behavior.

In another example, a system 300 for assessing operator behavior during a medical procedure involving medical equipment 110, 120, 130, 140, is provided. The system includes one or more processors 310 configured to:

receive S110 operator interaction data 150 representing operator interactions 160 with the medical equipment during the medical procedure;

input S120 the operator interaction data 150 into a neural network 170, the neural network being trained to generate a latent space encoding 180 of the operator interaction data; and output S130 a characteristic of the operator behavior based on a position of the latent space encoding 180 of the operator interaction data generated by the neural network 170, with respect to a distribution 190$_1$, 190$_2$ of latent space encodings of training data representing operator interactions with the medical equipment having known characteristics 200$_1$, 200$_2$ of the operator behavior.

It is noted that in the examples described above, the system 300 may also include medical equipment, such as for example medical imaging equipment 110, a contrast agent injector 120, a patient bed 130, and a monitor 140 for displaying medical images, and so forth. The system 300 may also include one or more user interface devices (not illustrated in FIG. 2) for generating operator interaction data 150 representing operator interactions with the medical equipment, such as a keyboard, a mouse, a touchscreen, and so forth.

The above examples are to be understood as illustrative of the present disclosure, and not restrictive. Further examples are also contemplated. For instance, the examples described in relation to computer-implemented methods, may also be provided by the computer program product, or by the computer-readable storage medium, or by the system 300, in a corresponding manner. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an"

does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A computer-implemented method of providing an assessment of operator behavior during a medical procedure involving medical equipment, comprising:

receiving by at least one processor, during the medical procedure, operator interaction data representing operator interactions with a user interface device associated with the medical equipment;

inputting by the at least one processor the operator interaction data into a trained machine-learning model;

in response to the inputting, generating by the least one processor, a latent space encoding of the operator interaction data; and outputting by the at least one processor, as the assessment of the operator behavior, a characteristic of a set of known characteristics of the operator behavior, based on a position of the latent space encoding of the operator interaction data, with respect to a distribution of latent space encodings of training data representing operator interactions with the user interface device, the distribution being associated with one of the set of known characteristics of the operator behavior.

2. The computer-implemented method of claim 1, wherein the operator interactions represent one or more of:

setting by the at least one processor, through the user interface, a value of a parameter of the medical equipment used during the medical procedure, and setting by the at least one processor, through the user interface, a value of an image visualization parameter for an image generated by the medical equipment.

3. The computer-implemented method according to of claim 1, wherein the set of known characteristics of the operator behavior includes one or more characteristics selected from the group: target behavior, typical behavior, fatigued behavior, inexperience, and unexpected behavior.

4. The computer-implemented method according to of claim 1, wherein the training data comprises performance data for each of a plurality of sets of operator interactions, and wherein the known characteristics of the operator behavior are assigned to the distributions of latent space encodings of the training data based on the performance data for a corresponding set of interactions.

5. The computer-implemented method of claim 1, wherein the latent space encodings of the training data are clustered to provide a distribution of latent space encodings for each of one or more known characteristics of the operator behavior; and wherein the outputting a characteristic of the operator behavior based on a position of the latent space encoding of the operator interaction data, with respect to a distribution of latent space encodings of training data representing operator interactions with the medical equipment having known characteristics of the operator behavior, comprises:

determining by the at least one processor a distance between the latent space encoding of the inputted operator interaction data and a centroid of the distribution of the latent space encodings for each of the one or more known characteristics of the operator behavior; and outputting by the at least one processor, as the characteristic of the operator behavior, the characteristic of the operator behavior for the distribution having a centroid with the shortest distance from the latent space encoding for the inputted operator interaction data.

6. The computer-implemented method of claim 1, wherein the method further comprises:

receiving by the at least one processor medical equipment identification data representing a type of the medical equipment used during the medical procedure; and wherein the outputting a characteristic of the operator behavior is based further on the received medical equipment identification data.

7. The computer-implemented method of claim 1, wherein the machine-learning model is trained to generate the latent space encoding of the operator interaction data based further on peripheral hardware data generated during the medical procedure; and wherein the method further comprises:

receiving by the at least one processor peripheral hardware data generated during the medical procedure;

inputting by the at least one processor the peripheral hardware data into the machine-learning model; and wherein the outputting a characteristic of the operator behavior based on a position of the latent space encoding of the operator interaction data, is based further on the inputted peripheral hardware data.

8. The computer-implemented method of claim 1, wherein the received operator interaction data represents a first type of interaction selected from the group: setting a value of a parameter of the medical equipment used during the medical procedure, and setting a value of an image visualization parameter for an image generated by the medical equipment, and wherein the machine-learning model is trained to generate a latent space encoding of the operator interaction data for the first type of interaction;

and wherein the method further comprises:

receiving by the at least one processor operator interaction data representing a second type of interaction selected from the group: setting a value of a parameter of the medical equipment used during the medical procedure, and setting a value of an image visualization parameter for an image generated by the medical equipment, the second type of interaction being different to the first type of interaction;

inputting by the at least one processor the operator interaction data representing the second type of interaction into a second machine-learning model, the second machine-learning model being trained to generate a latent space encoding of the operator interaction data for the second type of interaction; and wherein the outputting a characteristic of the operator behavior is based on:

the position of the latent space encoding of the operator interaction data for the first type of interaction, with respect to the distribution of latent space encodings generated from training data representing operator interactions for the first type of interaction with the medical equipment having known characteristics of the operator behavior; and the position of the latent space encoding of the operator interaction data for the second type of interaction, with respect to the distribution of latent space encodings generated from training data representing operator interactions for the second type of interaction with the medical equipment having known characteristics of the operator behavior.

9. The computer-implemented method of claim 1, wherein the received operator interaction data represents a first type of interaction selected from the group: setting a value of a parameter of the medical equipment used during the medical procedure, and setting a value of an image visualization parameter for an image generated by the medical equipment, and wherein the machine-learning model is trained to generate a latent space encoding of the operator interaction data for the first type of interaction;

and wherein the method further comprises:

receiving by the at least one processor operator interaction data representing a second type of interaction selected from the group: setting a value of a parameter of the medical equipment used during the medical procedure, and setting a value of an image visualization parameter for an image generated by the medical equipment, the second type of interaction being different to the first type of interaction;

inputting by the at least one processor the operator interaction data representing a second type of interaction into a second machine-learning model, the second machine-learning model being trained to generate a latent space encoding of the operator interaction data for the second type of interaction; and wherein the outputting a characteristic of the operator behavior is based on a position of a weighted latent space encoding with respect to a weighted distribution of latent space encodings generated from training data representing operator interactions including the first type of interaction and the second type of interaction with the medical equipment and having known characteristics of the operator behavior, and wherein the weighted latent space encoding is determined by combining:

a weighting of the latent space encoding of the operator interaction data for the first type of interaction; and a weighting of the latent space encoding of the operator interaction data for the second type of interaction.

10. The computer-implemented method of claim 1, wherein the receiving, the inputting, and the outputting, are performed for operator interaction data that is generated over a plurality of different time intervals.

11. The computer-implemented method of claim 1, further comprising:

outputting by the at least one processor a graphical representation of the position of the latent space encoding of the operator interaction data, with respect to the distribution of latent space encodings generated from training data representing operator interactions with the medical equipment having known characteristics of the operator behavior; and/or calculating by the at least one processor a confidence value for the latent space encoding and outputting the confidence value; and/or outputting by the at least one processor a warning based on the outputted assessment of the operator behavior.

12. The computer-implemented method of claim 1, wherein the machine-learning model is trained to generate the latent space encoding of the operator interaction data, by:

receiving by the at least one processor training data representing a plurality of sets of operator interactions with the medical equipment;

inputting by the at least one processor the training data into the machine-learning model; and for each of a plurality of the sets of operator interactions:

generating a latent space encoding of the inputted training data using the machine-learning model;

reconstructing the inputted training data from the latent space encoding using the machine-learning model; and adjusting parameters of the machine-learning model based on a difference between the inputted training data and the reconstructed inputted training data.

13. The computer-implemented method of claim 9, wherein the machine-learning model and the second machine-learning model are trained to generate the latent space encoding of the operator interaction data, by:

receiving by the at least one processor training data representing a plurality of sets of operator interactions with the medical equipment, the operator interactions representing the first type of interaction and the second type of interaction;

inputting by the at least one processor the training data representing the first type of interaction into the machine-learning model;

inputting by the at least one processor the training data representing the second type of interaction into the second machine-learning model; and for each of a plurality of the sets of operator interactions:

generating a latent space encoding of the inputted training data representing the first type of interaction using the machine-learning model;

generating a latent space encoding of the inputted training data representing the second type of interaction using the second machine-learning model;

applying weightings to the latent space encodings of the operator interaction data to provide a combined latent space encoding of the operator interaction data;

reconstructing the inputted training data representing the first type of interaction from the combined latent space encoding;

reconstructing the inputted training data representing the second type of interaction from the combined latent space encoding using the second machine-learning model; and adjusting the applied weightings and the parameters of the machine-learning model and the second machine-learning model, based on a difference between the inputted training data and the reconstructed inputted training data.

14. The computer-implemented method of claim 13, wherein the training data represents a plurality of sets of operator interactions with the medical equipment for a group of users; and wherein the method of assessing operator behavior during a medical procedure involving medical equipment comprises:

outputting by the at least one processor the characteristic of the operator behavior based on the position of the latent space encoding of the operator interaction data generated by the machine-learning model, with respect to the distribution of latent space encodings of training data representing operator interactions with the medical equipment having known characteristics of the operator behavior for the group of users.

15. The computer-implemented method according of claim 13, wherein:

the training data represents a plurality of sets of operator interactions with the medical equipment for a batch of one or more users; and wherein the method further comprises performing the inputting the training data into the machine-learning model, and the repeating the generating, the reconstructing, and the adjusting, using sets of operator interactions for each of a plurality of different batches of one or more users to provide a plurality of corresponding machine-learning models, each being trained using the training data for a different batch of users; and wherein the method of assessing operator behavior during a medical procedure involving medical equipment comprises performing the inputting the operator interaction data into a machine-learning model having parameters that are determined based on a combination of the parameters from the machine-learning model trained using the training data for a plurality of different batches of one or more users.

\* \* \* \* \*